United States Patent [19]

Jansons

[11] Patent Number: 4,474,990

[45] Date of Patent: Oct. 2, 1984

[54] PREPARING P-PHENOXY BENZOYL COMPOUNDS

[75] Inventor: Viktors Jansons, Los Gatos, Calif.

[73] Assignee: Raychem Corporation, Menlo Park, Calif.

[21] Appl. No.: 444,420

[22] Filed: Nov. 24, 1982

Related U.S. Application Data

[63] Continuation of Ser. No. 281,527, Jul. 8, 1981, abandoned.

[51] Int. Cl.$^3$ .............................................. C07C 45/46
[52] U.S. Cl. .................................. 568/319; 568/322; 562/419
[58] Field of Search ...................... 568/319, 322, 323; 528/179, 193, 266, 207; 562/419

[56] References Cited

U.S. PATENT DOCUMENTS

| | | | |
|---|---|---|---|
| T970,006 | 5/1978 | Rose | 568/322 |
| 1,930,449 | 10/1933 | Bruson et al. | 562/419 |
| 2,861,102 | 11/1958 | Huff et al. | 562/419 |
| 3,764,583 | 10/1973 | Newton et al. | 260/47 R |
| 3,953,400 | 4/1976 | Dahl | 528/179 |
| 4,079,075 | 3/1978 | Lee et al. | 562/419 |

*Primary Examiner*—James H. Reamer
*Attorney, Agent, or Firm*—Edith A. Rice; Herbert G. Burkard

[57] ABSTRACT

Substantially pure p-phenoxybenzoyl compounds are prepared by reacting diphenyl ether and an appropriate acyl compound in the presence of hydrogen fluoride. The resulting p-phenoxyaryl alkyl ketone can be converted into p-phenoxybenzoic acid or salts thereof, p-phenoxybenzoyl halide or lower alkyl p-phenoxybenzoate for use preparing homo- and copolymers containing a p-phenoxybenzoyl repeating unit.

14 Claims, No Drawings

PREPARING P-PHENOXY BENZOYL COMPOUNDS

This application is a continuation of application Ser. No. 281,527, filed July 8, 1981 now abandoned.

BACKGROUND OF THE INVENTION

This invention relates to the preparation of substantially pure p-phenoxybenzoyl compounds.

U.S. Pat. No. 3,953,400 to K. J. Dahl, Apr. 27, 1976, teaches the preparation of poly(arylene ether ketones) by polymerizing a p-phenoxybenzoyl moiety-containing monomer in the presence of a hydrogen fluoride-boron trifluoride catalyst and a capping agent. The monomer can be, for example, a p-phenoxybenzoyl halide, p-phenoxybenzoic acid or $C_1$–$C_3$ alkyl p-phenoxybenzoates. The polymer produced by the process described in U.S. Pat. No. 3,953,400 contains the p-phenoxybenzoyl repeating unit having the structure

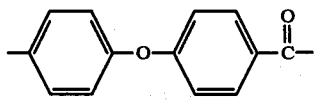

The polymer has a tensile elongation to break of at least about 50% at room temperature and a main inherent viscosity within the range from about 0.8 to about 1.65. It has been found that in order to obtain satisfactory polymer product using the process described in the Dahl patent, substantially pure p-phenoxybenzoyl monomer must be used. The presence of even small amounts of impurities interferes with the polymerization process.

SUMMARY OF THE INVENTION

This invention is based on the discovery that substantially pure p-phenoxybenzoyl compounds can be prepared by Friedel-Crafts acylation of diphenyl ether using hydrogen fluoride as the catalyst.

This invention comprises a method for the preparation of p-phenoxybenzoyl compounds of the formula

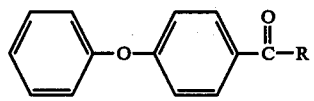

wherein R is lower alkyl by reacting diphenyl ether with an acyl compound of the formula

wherein R is lower alkyl and $R^1$ is selected from the group consisting of halogen, hydroxyl, —$OR^2$ and

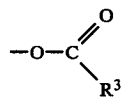

where $R^2$ and $R^3$ are each lower alkyl, in the presence of hydrogen fluoride.

The resulting p-phenoxyphenyl alkyl ketone can be converted to the corresponding acid, acid salt, acid halide or lower alkyl p-phenoxybenzoate, that is, compounds of the formula

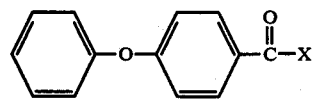

wherein X is halogen, hydroxyl, lower alkoxy or —OM where M is a metal ion, by known methods. Substantially pure p-phenoxybenzoyl compounds are obtained and are useful as monomers for preparing polymers containing a p-phenoxybenzoyl repeating unit.

DETAILED DESCRIPTION OF THE INVENTION

In accordance with this invention, diphenyl ether is reacted with an acyl compound of the formula

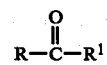

to produce corresponding p-phenoxyphenyl alkyl ketone of the formula

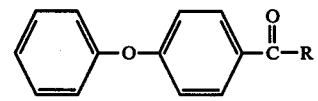

wherein R and $R^1$ are as defined above.

In the above definitions, the term "lower alkyl" refers to alkyl radicals containing 1 to 4 carbon atoms, i.e. methyl ethyl, propyl, and butyl. The term "lower alkoxy" refers to include alkoxy radicals containing from 1 to 4 carbon atoms, i.e., methoxy, ethoxy, propoxy and butoxy. Halogen refers to fluorine, chlorine, bromine and iodine. The metal ion, M, can be any metal ion but is preferably sodium, potassium or calcium.

The acyl compound reacted with diphenyl ether can be, for example, acetic acid, acetic anhydride, acetyl chloride, acetyl fluoride, methyl, ethyl, propyl or butyl acetate, propionic acid, anhydride, acid halide, or ester or butyric acid, anhydride, acid halide or ester. Other compounds which would form the acid in situ in the reaction medium, for example sodium acetate, can also be used and such compounds are considered to be included in the acyl compound.

The reaction of diphenyl ether with the acyl compound is carried out in the presence of hydrogen fluoride. The amount of hydrogen fluoride present should be at least about 30 percent by weight, based on the total weight of the reactants. Preferably, hydrogen fluoride is present in an amount of about 50 percent to about 100 percent by weight based on the weight of the reactants. Additional hydrogen fluoride can be used if desired, but no advantage is derived from doing so. In general, the amount of hydrogen fluoride used should be in substantial molar excess of the total molar quantity of basic species present in the system. If less than 30 percent hydrogen fluoride is used, the reaction will not proceed to completion and relatively low yields of ketone will be obtained. Conducting the reaction at higher temperatures may result in driving the reaction to completion under such conditions.

An inert diluent can be present if desired. Suitable inert diluents are, for example, normal alkanes containing 3 to 10 carbon atoms and germinal polychloro-, polyfluoro- and poly(fluorochloro)-n-alkanes containing 1 to 10 carbon atoms, sulfur dioxide, sulfolane, and the like.

In general, the reaction can be conducted at temperatures in the range of from about −20° to about +70° C., preferably from about −20° to about +40° C. and most preferably from about −10° to about −30° C. The reaction is preferably carried out under atmospheric pressure or the normal vapor pressure of hydrogen fluoride. Greater or less pressure can be applied, if desired.

The reaction of diphenyl ether with the acyl compound in the presence of hydrogen fluoride produces very high yield of mono-acylated para-isomer. Unlike similar reactions using traditional Friedel-Crafts catalysts, such as aluminum trichloride, there is little, if any tendency for diacylation to occur. Further, there is minimal, if any, other impurities in the reaction product. The high yield and high purity of the ketone produced makes it particularly suited for use in preparing monomers for formation of poly(arylene ether ketones).

The p-phenoxyphenyl alkyl ketone can be converted by known precedures to the corresponding acid, acid salt, acid halide or ester, i.e. to a compound of the formula

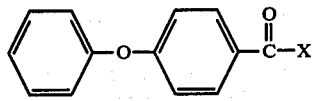

wherein X is halogen, hydroxyl, lower alkoxy or —OM, where M is a metal ion. The resulting substantially pure, p-phenoxybenzoyl compounds can be used as monomers in the preparation of poly(arylene ether ketones).

For example, p-phenoxyacetophenone can be oxidized by reaction with sodium or potassium hypochlorite to give the sodium or potassium salt of p-phenoxybenzoic acid which can then be acidified, e.g., by addition of hydrochloric acid, to yield p-phenoxybenzoic acid.

Alternate methods of oxidation of p-phenoxyacetophenone include air oxidation in the presence of a catalyst such as cobalt (II) acetate bromide together with manganese (II) acetate, or manganese acetate and manganese dioxide or oxidation in the presence of an oxidizing agent such as potassium permanganate or with sodium dichromate in acid solution.

The acid or its salts can be readily converted into the acid chloride by reaction with thionyl chloride or phosgene in the presence of N,N-dimethyl formamide catalyst. The corresponding esters can be prepared by reacting the acid or acid salt with an alcohol in the presence of an acid catalyst.

The p-phenoxybenzoyl compounds prepared in accordance with this invention can be polymerized to yield polymers having the repeating unit

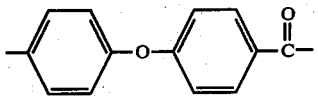

using known polymerization procedures. Preferred methods of producing such polymers are disclosed in U.S. Pat. Nos. 3,953,400, 4,229,564, 4,239,884 and 4,247,682, the disclosures of which are hereby incorporated by reference. As discussed in these patents, homopolymers and copolymers of p-phenoxybenzoyl containing monomers can be prepared.

In the preparation of copolymers, a wide variety of comonomers can be employed. Suitable comonomers include, for example, p-(phenylthio)benzoyl chloride, m-phenoxybenzoyl chloride, 2-dibenzofurancarbonyl chloride, 2-thianthrenecarbonyl chloride, 2-phenoxathiincarbonyl chloride, 2-phenodioxincarbonyl chloride, 2-dibenzothiophenecarbonyl chloride, 4(4'-biphenyloxy)benzoyl chloride, 4-(1' naphthoxy)benzoyl chloride, 4-(2' naphthoxy)benzoyl fluoride, terphenyl carbonyl chloride, quaterphenyl carbonyl fluoride and the like.

In the following examples, p-phenoxyacetophenone is produced by reacting diphenyl ether with an acetylation agent, specifically, acetic anhydride, acetyl chloride or acetic acid. In Examples 1–8, the reaction is conducted in the presence of hydrogen fluoride in accordance with this invention. In each case, the product is analyzed for the presence of a diacylation product and impurities and the yield determined. Example 9, a comparative example in which p-phenoxyacetephenone is produced by reacting diphenyl either with acetic anhydride in the presence of aluminum trichloride, a traditional Friedel-Crafts catalyst. In example 10, p-phenoxyacetephenone produced in accordance with this invention is oxidized to yield p-phenoxybenzoic acid suitable for use as a monomer.

EXAMPLE 1

To a frozen solution of 1.70 g. (0.010 mole) diphenyl ether in 1.30 g. (0.012 mole; a 20 mole % excess) acetic anhydride, was added 3.0 ml anhydrous hydrogen fluoride (50% by weight of reactants). A magnetic stirrer was added and the reaction mixture was stirred magnetically and degassed several times while warming to 24° C. in air, and stirred for 18 hours at 24° C. The resultant red solution was poured into a plastic beaker and allowed to evaporate in an air stream/24° C., leaving a crystalline residue. This was crushed in ca 30 ml ice water, collected by filtration, partly air dried and further dried at 40° C. under a vacuum for about 2 hours, yielding 2.0 g. (94.2%) of nearly colorless crystals with a yellow tinge. Analysis showed only 0.73% unreacted diphenyl ether or 99.25% yield of p-phenoxyacetophenone by gas-liquid chromatography GLC. Thin layer chromatography (TLC) showed a very weak fast moving impurity spot corresponding to diphenyl ether while no trace of a slower moving spot which would correspond to a diacylation product was observed. The product had a melting point of 47°–50° C.

EXAMPLES 2–8

The procedure described in Example 1 was repeated using diphenyl ether in the amounts specified in the following Table with an acetylation agent, namely acetic anhydride, acetic acid or acetyl chloride as identified in the Table and in the amount specified. The reaction was conducted in the presence of hydrogen fluoride in the amounts specified in the Table. In Examples 3, 5, 6, 7 and 8, the reaction was conducted at 24° C. for about 24 hours. In Example 2, the temperature of the reaction ranged from −10° C. to +10° C. and the reaction took place over 39 hours. In Example 4, the reaction was conducted at 24° C. for 66 hours. In each example the product was analyzed by gas-liquid chromatography and the yield determined by calculation on a weight percent basis and by gas-liquid chromatography. The results are reported in the Table. Each product was also analyzed for the presence of diacylation product by thin-layer chromatography. In each case no evidence of diacylation product was observed. A fast moving spot indicating unreacted diphenyl ether was observed in each case.

As indicated in the Table, Example 8 resulted in incomplete reaction. This is believed to be due to the relatively low amound of hydrogen fluoride used (32.5% by weight based on the weight of the reactants).

EXAMPLE 9

This is a comparative example in which p-phenoxyacetophenone is prepared by reaction of diphenyl ether and acetic anhydride in the presence of a traditional Friedel-Crafts Catalyst, aluminum trichloride.

To a cooled (2°-10° C.), stirred solution of 17.02 g. (0.100 mole) diphenyl ether, 10.21 g. (0.100 mole) acetic anhydride and 50 ml methylene dichloride was gradually added 29.87 g. (o. 224 mole) anhydrous aluminum trichloride under a nitrogen atmosphere over a half hour period. The reaction mixture was heated at 43° C. (reflux) for an hour, then allowed to cool to room temperature (24° C.) and then poured on stirred ice. The resulting yellow oil was extracted with methylene dichloride, dried over anhydrous magnesium sulfate, filtered and the solvent removed by evaporation at 24° C. The resulting orange syrup was dried at 80° C. under a reduced pressure of 0.1 mm mercury to yield 19.66 g. (93%) orange melt that crystallized on cooling. The product had a melting point of 40°-45° C. The product was analyzed by gas-liquid chromatography and the results are reported in the Table. Thin-layer chromatography resulted in two slow moving impurity spots indicating formation of a diacylation product.

EXAMPLE 10

In this example, p-phenoxyacetephenone produced in accordance with Example 2 in the presence of hydrogen fluoride and p-phenoxyacetephenone produced in accordance with Example 9 in the presence of aluminum trichloride were each converted into benzoic acid.

In each case a 5.25% sodium hypochlorite solution (85.1 g.: 0.060 mole) was added slowly in portions to a solution of 3.18 g. (0.0150 mole) the p-phenoxyacetophenone sample while heating from 40° to 100° C. The resulting solution was concentrated at 100° C., producing a crystalline precipitate. Acetone was then added to consume excess sodium hypochlorite followed by boiling, acidification with some excess concentrated hydrochloric acid (10 ml of 12N), stirring, filtration, water wash and then drying at 70° C./under vacuum for about 1 hr. The p-phenoxybenzoic acid obtained from the p-phenoxyacetephenone produced in the presence of hydrogen fluoride was white with a melting point of 159°-162° C. In contrast, the p-phenoxybenzoic acid produced in the presence of aluminum trichloride had a yellow (or light beige) discoloration and a strongly depressed melting point of 137°-149° C., indicating presence of considerable impurities.

Once given the above disclosure, many other features, modifications, and improvements will become apparent to one skilled in the art. Such other features, modifications and improvements are, therefore, considered a part of this invention, the scope of which is to be determined by the following claims.

What is claimed is:

1. A methed for the preparation of p-phenoxybenzoyl compounds of the formula

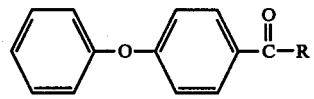

wherein R is lower alkyl, which comprises the monoacylation of diphenyl ether by reacting diphenyl ether with an acyl compound of the formula

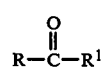

TABLE

| Example No. | Acetyl Chloride g (Moles) | Acetic Anhydride g (Moles) | Acetic Acid g (Moles) | Diphenyl Ether g (Moles) | Catalyst HF ml (Wt %) | Catalyst AlCl₃ + CH₂Cl₂ g (mol.) | Gas-Liquid Chromatography (GLC) Diphenyl Ether (%) | Diacylation (%) | Impurities (%) | Yield % by wt. | Yield % by GLC |
|---|---|---|---|---|---|---|---|---|---|---|---|
| 1 | — | 1.30 (0.012) | — | 1.70 (0.010) | 3.0 (50) | — | 0.70 | 0 | 0.017 | 94.2 | 99.3 |
| 2 | — | 929.2 (9.10) | — | 1549.0 (9.10) | 3400 (57.8) | — | 11.0 | 0 | 0.04 | 96 | 89 |
| 3 | — | — | 1.44 (0.024) | 3.40 (0.02) | 10 (67) | — | 26.8 | 0 | 0.03 | — | 73 |
| 4 | — | — | 1.44 (0.024) | 3.40 (0.02) | 10 (67) | — | 13.8 | 0 | 0.107 | 80 | 86 |
| 5 | 7.94 (0.101) | — | — | 17.02 (0.10) | 33 (57) | — | 0.80 | 0 | 0.01 | 96.0 | 99.2 |
| 6 | 1.21 (0.0154) | — | — | 2.17 (0.0128) | 3.0 (47) | — | 0.99 | 0 | 0.02 | 84.5 | 98.9 |
| 7 | 1.41 (0.018) | — | — | 2.55 (0.015) | 1.7 (30) | — | 27.5 | 0 | 0.038 | — | 72.5 |
| 8 | 7.94 (0.101) | — | — | 17.09 (0.10) | 12 (32.5) | — | * | * | * | * | * |
| 9 | — | 10.21 (0.10) | — | 17.02 (0.10) | — | 29.87 (0.224) | 1.76 | 0.80 | 0.23 | 93 | 97.4 |

*Incomplete reaction - yield estimated to be 70% by thin-layer chromatography wherein R is lower alkyl and $R^1$ is selected from the group consisting of halogen, hydroxyl, $-OR^2$ and $$-O-\overset{O}{\underset{R^3}{C}}$$

where $R^2$ and $R^3$ are each lower alkyl, in the presence of hydrogen fluoride as the sole catalyst for the reaction, to obtain the mono-acylated, para isomer.

2. A method in accordance with claim 1, wherein hydrogen fluoride is present in an amount of at least 30 percent by weight based on the weight of diphenyl ether and acyl compound.

3. A method in accordance with claim 2, wherein said hydrogen fluoride is present in an amount of at least 50% by weight based on the total weight of the diphenyl ether and acyl compound.

4. A method in accordance with claim 1, wherein said reaction is conducted at a temperature in the range of from about $-20°$ to about $+70°$ C.

5. A method in accordance with claim 1, wherein said reaction is conducted at a temperature in the range of from about $-10°$ to about $-30°$ C.

6. A method for the preparation of substantially pure p-phenoxyacetophenone which comprises reacting diphenyl ether with an acyl compound selected from the group consisting of acetyl chloride, acetic acid and acetic anhydride in the presence of hydrogen fluoride.

7. A method in accordance with claim 6, wherein said acyl compound is acetyl chloride.

8. A method in accordance with claim 6, wherein said acyl compound is acetic acid.

9. A method in accordance with claim 6, wherein said acyl compound is acetic anhydride.

10. A method in accordance with claim 6, wherein hydrogen fluoride is present in an amount of at least 30 percent by weight based on the weight of diphenyl ether and acyl compound.

11. A method in accordance with claim 10, wherein said hydrogen fluoride is present in an amount of at least 50% by weight based on the total weight of the diphenyl ether and acyl compound.

12. A method in accordance with claim 6, wherein said reaction is conducted at a temperature in the range of from about $-20°$ to about $+70°$ C.

13. A method in accordance with claim 12, wherein said reaction is conducted at a temperature in the range of from about $-10°$ to about $+30°$ C.

14. A method of preparing substantially pure p-phenoxybenzoic acid which comprises reacting diphenyl ether with an acyl compound of the formula $$R-\overset{O}{\underset{\|}{C}}-R^1$$

wherein R is lower alkyl and $R^1$ is selected from the group consisting of halogen, hydroxyl, $-OR^2$ and $$-O-\overset{O}{\underset{R^3}{C}}$$

where $R^2$ and $R^3$ are each lower alkyl, in the presence of hydrogen fluoride as the sole catalyst for the reaction, to produce a compound of the formula

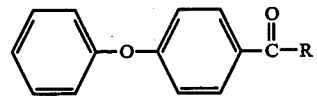

wherein R is lower alkyl, and then oxidizing the compound produced to yield substantially pure p-phenoxybenzoic acid.

* * * * *